United States Patent [19]

Montes

[11] Patent Number: 5,017,587

[45] Date of Patent: May 21, 1991

[54] TREATMENT OF PLANTAR WARTS USING CYCLOHEXIMIDE

[76] Inventor: Leopoldo F. Montes, Buenos Aires, Argentina, 1121

[21] Appl. No.: 464,173

[22] Filed: Jan. 12, 1990

[51] Int. Cl.$^5$ .............................................. A61K 31/445
[52] U.S. Cl. ..................................... 514/328; 514/889
[58] Field of Search ................................ 514/317, 328

[56] References Cited

U.S. PATENT DOCUMENTS 3,670,084 6/1972 Montes .................................. 424/268
4,427,684 1/1984 Ores ..................................... 514/728
4,557,934 12/1985 Cooper ................................. 514/159

OTHER PUBLICATIONS

Montes, *J. Cutaneous Pathol.*, 3:1-4, 1976.

*Primary Examiner*—Glennon H. Hollrah
*Assistant Examiner*—Gary E. Hollinden
*Attorney, Agent, or Firm*—Darby & Darby

[57] ABSTRACT

The invention consists in healing of plantar warts with cycloheximide. Cycloheximide is used in various topical forms and methods of application to treat plantar warts. The concentrations employed ranges from 0.01% to 5.0% and the duration of treatment from 5 to 12 weeks.

5 Claims, No Drawings

TREATMENT OF PLANTAR WARTS USING CYCLOHEXIMIDE

SUMMARY OF THE INVENTION

The invention consists in a method for the treatment of plantar warts in which cycloheximide with a suitable carrier is applied over the warts during a certain period and also the composition for the treatment of plantar warts.

DESCRIPTION OF PLANTAR WARTS

Plantar warts also known as verruca plantaris result from the invasion and subsequent colonization of the stratum corneum by a human papillomavirus (HPV). Among the 30 or more different types of HPV, the HPV 1 seems to be the one which causes plantar warts (Cance, D. J. and Gardner, S. D. Papovavirus: Papillomaviruses and Polyomaviruses, Page 483 in Principles and Practice of Clinical Virology, Edited by Zuckerman, A. J., Banatvala, J. E. and Pattison, J. R., John Wiley & Sons Ltd., New York, 1987).

The viral infection produces thickening of the epidermis, also known as acanthosis, and the human host reacts with an inflammatory infiltrate in the upper dermis. As plantar warts grow, the surface of the involved skin becomes harder and harder leading to the formation of a callus. Pressure on this callus while walking produces pain, sometimes unbearable, but the callus also acts as a protective shield against the penetration of topical treatments.

Plantar warts vary in size from small punctiform lesions to large plaques which may involve the entire sole. The plaque type of plantar wart is often referred to as mosaic wart.

DESCRIPTION OF PRIOR ART

Treatment of plantar warts is one of the greatest challenges defying the skill and knowledge of dermatologists. Because the available treatments are unsatisfactory, I agree with Shelley who stated that "despite our wealth of understanding concerning the nature of warts, therapeutically we are still uncomfortably close to the brimstone treatment that Turner described in his treatise on dermatology way back in 1723". (Shelley, W. B., Consultations in Dermatology, Vol. I, Page 12, W. B. Saunders Company, Philadelphia, 1972)

The variety of known treatments may be summarized as follows:
A. Keratolytic Agents: salicylic acid, phenol, nitric acid, lactic acid, trichloracetic acid, formalin, glutaraldehyde, cantharidin, podophyllin.
B. Physical Agents: Liquid Nitrogen, Carbon Dioxide, X Ray therapy, Radium Therapy, Laser Systems.
C. Surgical Methods: Excision, Curettage, Electrosurgery, Cryosurgery.

DESCRIPTION OF THE INVENTION

The two facts that lead to the discovery of the method of the invention were:
A. The Surprising Prolonged and Complete Adhesion of Flexible Fabric Bandages (FFB) to the Sole.

For use in dermatology a different type of adhesive bandage became available. It consists of a stretchable fabric which replaces the standard plastic in the so-called "Band-Aid". "Curad" or "Rite-Aid", to name some of the most popular bandages. This fabric stretches to stay on bendable places ("moves and flexes with you"). In addition, the unique open-weave design lets the skin breathe, stays on even when wet and acts as a cushion pad.

In the daily management of skin diseases the greatest usefulness of FFB has been its use on the soles where older types of bandages were not capable to stay on for a long time without coming loose. Thus they have become an invaluable tool for covering traumatic and surgical wounds or lesions on the sole.

B. The Use of FFB for Isolation of Fungus and the Unexpected Healing of a Plantar Wart.

One of the challenges while dealing with athlete's foot is the recovery of large enough numbers of fungi from the dry lesions in the sole to allow quantification of fungal cells. This procedure is not usually performed by clinical dermatologists being essentially a research method.

One of the patients in treatment due to athlete's foot involving most of the soles in addition had been suffering from a plantar wart so stubbornly resistant to all forms of treatment for a period of seven years, that he had abandoned its medication. In order to isolate, for a mycological investigation, a large number of fungi, an FFB impregnated with Mycosel was applied on the sole, which is a culture medium employed for recovery of fungi. The Mycosel-impregnated FFB was left in place for 24 hours and used afterwards to inoculate Petri dishes. Following removal of the FFB, a new Mycosel-impregnated FFB was reapplied and the procedure repeated every day for seven consecutive days to obtain a daily harvest of fungi.

When the patient returned four weeks later, he unexpectedly indicated that the plantar wart which had been also covered by the FFB had dissapeared. Thus it could be inferred that Mycosel could somehow have influenced the cure of the plantar wart.

After this finding, I began using the same method of impregnating FFB with Mycosel, allowing it to remain for 10 consecutive days on plantar warts of five different patients. All warts disappeared within 4-6 weeks after completion of the treatment.

The next logical step was to determine which one of the ingredients in Mycosel might have exerted its action on the warts.

Mycosel's chemical formula is as follows:
Peptone: 1%
Dextrose: 1%
Agar: 1.55%
Cycloheximide: 0.04%
Chloramphenicol: 0.005%

Consequently, separate sets of FFB were employed which were individually impregnated with each one of the five ingredients of Mycosel at the same concentrations. These newly impregnated FFB were applied to warts of soles in twenty five different patients (five patients for each ingredient). Only the five patients treated with the FFB impregnated with cycloheximide showed cure of the plantar warts. The FFB were left on the wart surface for one week. Within 6-8 weeks after completion of the treatment, the warts were gone.

Cycloheximide, the active agent used in the method of the invention is commercially available as a whitish powder with an anhydrous molecular weight of 281.3. The chemical formula $C_{15}H_{23}NO_4$ is: 3-[2-(3,5-Dimethyl-2-oxocyclohexyl)-2-hydroxyethyl]-glutarimide. Its trade name is Acti-dione and it was first isolated from culture filtrates of *Streptomyces griseus.*

The following vehicles were used as carriers for cycloheximide:

(a) Petrolatum in its two forms: yellow petrolatum, or petroleum jelly, a purified mixture of semisolid hydrocarbons obtained from petroleum; white petrolatum, or white petroleum jelly, which is petrolatum wholly or nearly decolorized.

(b) Plastibase Hydrophilic TM, a vehicle containing by weight: 88.16% liquid petrolatum, 5.46% polyethylene, 6% emulsifying agent, 0.1% antioxidant and 0.1% preservative.

(c) Aquaphor TM, a stable, neutral, odorless, anhydrous ointment base miscible with water or aqueous solutions several times its own weight.

In order to achieve a uniform dispersion of cycloheximide in any of these vehicles, this compound was first placed in pure olive oil. This step took only a few minutes because after a little stirring of the mixture, cycloheximide appeared completely disolved into the olive oil. Afterwards, the mixture was added to any of the aforementioned vehicles and mechanically stirred with an electric agitator.

Suitable vehicles can also be Vaseline Petroleum Jelly TM or Vaseline TM.

Placing cycloheximide in any of those vehicles, the following concentrations were employed: 0.01%, 0.02%, 0.03%, 0.04%, 0.05%, 0.06%, 0.07%, 0.08%, 0.09%, 0.10%, 0.20%, 0.30%, 0.40%, 0.50%, 0.60%, 0.70%, 0.80%, 0.90%, 1%, 2%, 3%, 4% and 5%.

For the delivery of cycloheximide into the plantar warts several different methods were employed:

(a) Finger Cot Rubbing Procedure: direct rubbing of the wart applying the ointment with the index finger previously covered with a white latex tissue finger cot No. 88-2910 (Graham-Field, Hauppauge, N.Y.). The finger cot permits to avoid the simultaneous introduction of germs and/or contaminating materials and insures uniform pressure while rubbing. At the same time it facilitates quick penetration of the ointment into the stratum corneum. The rubbing is performed twice daily (every twelve hours).

(b) Cotton Swab Rubbing Procedure: rubbing with a cotton swab, also known as cotton-tipped applicator, commercially available in a steryle form (Diamond, abco, etc.). The cotton tip insures an even, rapid and complete penetration of the ointment into the stratum corneum invaded by the wart. The rubbing is also performed every twelve hours.

(c) Cycloheximide under FFB Occlusion: as described before the complete and prolonged adhesion of FFB is suitable for the delivery of cycloheximide ointment. After rubbing of the surface of the wart to insure elimination of surface bacteria of the normal skin flora, a FFB previously impregnated with cycloheximide ointment (approximately 0.5 gm) was applied to the surface of the wart. It is of interest that after treating many warts it was found that the butterfly shaped FFB adheres better than the standard rectangular shaped FFB. The application is repeated once daily, preferably after bedtime.

(d) Cycloheximide under FFB Oclusion after Cryosurgery: although cryosurgery has been advocated as a treatment for warts, in plantar warts is seldom, if ever, a completely curative procedure. Nevertheless, partial destruction of the plantar warts can be achieved through this technique. Consequently, mild freezing of the plantar warts with liquid nitrogen was also performed prior to the application of cycloheximide ointment.

(e) Cycloheximide under Tape Occlusion: using the procedure of application described under (c), plantar warts were treated with cycloheximide but instead of FFB, one of several adhesive tapes were employed to occlude the wart. The following tapes were used: Micropore TM surgical tape, Steri-Strip TM Skin Closure Tape, Dermiclear TM Tape, Transpore TM Surgical Tape, Water Proof Tape, Athleticare TM Sports Tape

EXAMPLES

The Table summarizes the patients treated thus far. In all cases there was gradual and steady reduction in size of the plantar wart or warts.

| | TOPICAL CYCLOHEXIMIDE IN PLANTAR WARTS: PATIENTS TREATED | | | | |
|---|---|---|---|---|---|
| Patient Number | Age | Sex | Size of Warts(s) ($cm^2$) | Concentration of Cycloheximide | Duration of Treatment |
| 1 | 15 | F | 1.0 | 0.01% | 8 weeks |
| 2 | 12 | M | 0.4 | 0.2% | 6 weeks |
| 3 | 24 | M | 2.0 | 0.1% | 6 weeks |
| 4 | 38 | F | 2.5 | 0.05% | 9 weeks |
| 5 | 42 | M | 1.7 | 0.3% | 8 weeks |
| 6 | 16 | F | 1.4 | 0.2% | 7 weeks |
| 7 | 21 | M | 1.8 | 0.02% | 6 weeks |
| 8 | 24 | M | 0.5 | 0.03% | 10 weeks |
| 9 | 32 | M | 3.0 | 0.04% | 9 weeks |
| 10 | 33 | F | 2.5 | 0.05% | 8 weeks |
| 11 | 64 | F | 0.9 | 0.06% | 9 weeks |
| 12 | 12 | F | 2.4 | 0.2% | 11 weeks |
| 13 | 42 | M | 1.5 | 0.2% | 10 weeks |
| 14 | 23 | M | 1.2 | 0.2% | 8 weeks |
| 15 | 54 | M | 0.7 | 0.2% | 8 weeks |
| 16 | 21 | F | 0.8 | 0.2% | 9 weeks |
| 17 | 39 | F | 2.1 | 0.2% | 7 weeks |
| 18 | 22 | M | 1.8 | 0.1% | 11 weeks |
| 19 | 55 | F | 1.6 | 0.5% | 10 weeks |
| 20 | 59 | M | 2.2 | 0.5% | 10 weeks |
| 21 | 48 | M | 2.8 | 0.4% | 7 weeks |
| 22 | 17 | F | 1.4 | 0.4% | 6 weeks |
| 23 | 47 | M | 2.0 | 0.2% | 8 weeks |
| 24 | 22 | F | 3.6 | 0.02% | 12 weeks |
| 25 | 33 | M | 1.5 | 1.0% | 9 weeks |
| 26 | 19 | F | 1.9 | 1.0% | 9 weeks |
| 27 | 29 | F | 1.0 | 1.0% | 9 weeks |
| 28 | 45 | M | 1.8 | 3.0% | 7 weeks |
| 29 | 41 | M | 2.8 | 4.0% | 6 weeks |
| 30 | 43 | F | 3.0 | 5.0% | 10 weeks |
| 31 | 20 | M | 1.5 | 1.0% | 5 weeks |
| 32 | 19 | M | 2.2 | 0.3% | 13 weeks |
| 33 | 18 | M | 3.2 | 0.3% | 12 weeks |
| 34 | 42 | F | 0.9 | 0.3% | 11 weeks |
| 35 | 27 | F | 2.8 | 0.2% | 15 weeks |
| 36 | 37 | M | 2.3 | 0.2% | 6 weeks |
| 37 | 50 | F | 1.9 | 0.2% | 6 weeks |
| 38 | 64 | M | 1.1 | 0.2% | 9 weeks |
| 39 | 40 | F | 2.1 | 0.4% | 6 weeks |
| 40 | 26 | M | 1.5 | 0.5% | 7 weeks |

The size in $cm^2$ Describes the total surface of the warts, the larger sizes usually indicating that there was more than one wart involved in a given patient. The reduction in the size of the wart continued until the wart completely disappeared. Most interesting, as the size of the wart diminished, the patients experienced a simultaneous reduction of pain while walking until the pain completely disappeared upon cure of the wart.

An additional observation was that the application of cycloheximide in any of its forms, did not result in irritation of the area nor any other side effect. This is important because many of the patients had previously experienced an unpleasant irritation from other agents which had been unsuccessful. All patients were required a pre-treatment period of two months without using any medications to insure that the effect evaluated was from cycloheximide alone.

Controls

Control observations were also performed in thirty patients using alone each one of the three vehicles mentioned above, without the incorporation of cycloheximide for periods ranging from 4-10 weeks. No cure of the plantar warts was observed. Ten patients were treated with each vehicle.

SCIENTIFIC DATA SUPPORTING THE EFFICACY OF THE METHOD

The family of viruses known as Papovaviridae is divided into two genera: the Polyomaviruses and the Papillomaviruses.

The virus which causes plantar warts belongs to the Papillomaviruses. Among the human Papillomaviruses or HPV they are classified as HPV types 1a, 1b and 1c (McCance, D. J. and Gardner, S. D., Papovaviruses. Chapter 13, Page 483. Principles and Practice of Clinical Virology. Edited by Zuckerman, A. J., Banatvala, J. E. and Pattison, J. R. John Wiley and Sons, Ltd. New York, 1987).

Because cultural methods for the "in vitro" isolation and growth of HPV have not yet become available, there is a lack of knowledge regarding specific antiviral HPV therapy.

Nevertheless, it is possible that cycloheximide may well have such an action because the HPV virion contains a double-stranded DNA molecule and cycloheximide markedly inhibits the synthesis of DNA (Bennett, Jr., L. L., Smithers, D and Ward, C. T. Inhibition of DNA Synthesis in Mammalian Cells by Actidione. Biochimica et Biophysica Acta 87:60-82, 1964).

Furthermore, it has been shown that cycloheximide enhances the production of interferon (Vilcek, J., Havell, E. A. and Kohase, M. Superinduction of Interferon with Metabolic Inhibitors: Possible Mechanisms and Practical Aplications. Antiviral with Clinical Potential. Edited by C. Merigan. Pages 22-29. The University of Chicago Press. Chicago, 1976). Interferon is a group of small proteins produced naturally by body cells in response to viral infections and other stimuli and it has been given as a treatment for various infections (Encyclopedia of Medicine. The American Medical Association. Pages 598-599. Random House. New York, 1989.) It is noteworthy that two types of cells known to produce interferon, namely leukocytes and fibroblasts are present in warts. Leukocytes, on one hand, are seen in biopsies of warts as they undergo involution (Pinkus, H. and Meheregan, A. H. A Guide to Dermatohistopathology. Pages 342-343. Appleton-Century Crofts. New York, 1981). Fibroblasts, on the other hand, are the most numerous cells in connective tissue (Montagna, W. and Parakkal, P. F. The Structure and Function of the Skin. Pages 118-121. Academic Press. New York, 1974) and connective tissue is particularly abundant in the thick dermis of the sole.

What I claim is:

1. A method of treating plantar warts which comprises the step of applying an effective amount of cycloheximide in a pharmaceutically acceptable topical carrier to the skin area affected by said warts to reduce the size of said warts.

2. The method according to claim 1 wherein said cycloheximide is applied at least once daily for periods between 5 to 12 weeks.

3. The method according to claim 1 wherein the concentration of cycloheximide is between about 0.01% and 5%.

4. The method of claim 1 which comprises freezing said warts with liquid nitrogen and thereafter applying cyclohexamide to said warts.

5. The method of claim 1 further comprising occluding said affected area with a bandage or tape after applying said cycloheximide.

* * * * *